(12) United States Patent
Mertelmeier et al.

(10) Patent No.: US 11,344,269 B2
(45) Date of Patent: May 31, 2022

(54) METHOD FOR MONITORING A TISSUE REMOVAL BY MEANS OF AN X-RAY IMAGING SYSTEM

(71) Applicant: Siemens Healthcare GmbH, Erlangen (DE)

(72) Inventors: Thomas Mertelmeier, Erlangen (DE); Ramyar Biniazan, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 338 days.

(21) Appl. No.: 16/580,055

(22) Filed: Sep. 24, 2019

(65) Prior Publication Data

US 2020/0100750 A1 Apr. 2, 2020

(30) Foreign Application Priority Data

Sep. 27, 2018 (EP) ..................... 18197165

(51) Int. Cl.
*A61B 6/00* (2006.01)
*A61B 6/03* (2006.01)
*A61B 6/04* (2006.01)

(52) U.S. Cl.
CPC .............. *A61B 6/502* (2013.01); *A61B 6/032* (2013.01); *A61B 6/4241* (2013.01); *A61B 6/547* (2013.01);

(Continued)

(58) Field of Classification Search
CPC ....... A61B 6/502; A61B 6/032; A61B 6/4241; A61B 6/547; A61B 6/0414; A61B 6/0435; A61B 6/482; G06T 2207/10116
See application file for complete search history.

(56) References Cited

U.S. PATENT DOCUMENTS

2016/0073988 A1* 3/2016 Nagai ................... A61B 6/482
378/62
2016/0113609 A1* 4/2016 Tsuyuki ................ A61B 6/482
600/425

(Continued)

FOREIGN PATENT DOCUMENTS

CA 2041664 A1 * 12/1990 ........... A61B 6/5235
DE 102015217141 A1 3/2017

(Continued)

OTHER PUBLICATIONS

Kalpana D Kariyappa et al.: "Contrast enhanced dual energy spectral mammogram, an emerging addendum in breast imaging", Nov. 2016; 89(1067): 20150609. Published online Oct. 5, 2016; doi: 10.1259/bjr.20150609.

(Continued)

*Primary Examiner* — Khai M Nguyen
(74) *Attorney, Agent, or Firm* — Harness, Dickey & Pierce, P.L.C.

(57) ABSTRACT

A method is for monitoring a tissue removal taking place via an X-ray imaging system. The method includes acquiring first X-ray projection scan data, influenced by a contrast medium, of the breast tissue situated in an image field of the X-ray imaging system. The contrast medium-influenced first X-ray projection scan data is generated with X-ray photons having a photon energy above an absorption edge of the contrast medium used. A first image data set is then reconstructed based upon the acquired X-ray projection scan data. Finally, based upon the reconstructed first image data set, the method includes determining a current position of the lesion, in relation to a reference coordinate system.

24 Claims, 3 Drawing Sheets

(52) U.S. Cl.
CPC ........... *A61B 6/0414* (2013.01); *A61B 6/0435* (2013.01); *A61B 6/482* (2013.01); *G06T 2207/10116* (2013.01)

(56) References Cited

U.S. PATENT DOCUMENTS

2016/0235380 A1* 8/2016 Smith .................... A61B 6/482
2017/0065241 A1   3/2017 Hoernig
2017/0245816 A1   8/2017 Flohr et al.

FOREIGN PATENT DOCUMENTS

| DE | 102016203257 A1 | 8/2017 |
|----|-----------------|--------|
| WO | WO 2015061582 A2 | 4/2015 |
| WO | WO 2017021919 A1 | 2/2017 |

OTHER PUBLICATIONS

European Extended Search Report for European Application No. 18197165.6 dated Apr. 4, 2019.

* cited by examiner

METHOD FOR MONITORING A TISSUE REMOVAL BY MEANS OF AN X-RAY IMAGING SYSTEM

PRIORITY STATEMENT

The present application hereby claims priority under 35 U.S.C. § 119 to European patent application number EP 18197165.6 filed Sep. 27, 2018, the entire contents of which are hereby incorporated herein by reference.

FIELD

Embodiments of the invention generally relate to a method for monitoring a tissue removal from breast tissue via of an X-ray imaging system. Thereby, image data influenced by a contrast medium is generated with the use of exclusively high-energy X-ray radiation.

BACKGROUND

Classic mammography plays an important part in the early identification of mammary carcinomas. In classic mammography, a fluoroscopic X-ray image is generated from a female or male breast. The X-ray radiation used thereby is weak radiation with an energy of approximately 25 to 35 keV. For the detection of the X-ray radiation, direct or indirect digital detectors are used in order to capture the emitted X-ray radiation. Direct digital detectors convert X-ray radiation directly into an electrical signal. Indirect digital detectors, however, first convert the X-ray radiation into visible light which is subsequently converted to an electrical signal. The X-ray recordings are observed on a special mammography diagnostic station which comprises one or two gray-scale monitors with which the X-ray images can be displayed.

It is disadvantageous that the sensitivity of classic mammography decreases with increasing breast density. In other words, lesions, in particular, tumors are identified less well with increasing tissue density. In addition, there are particular tumor types which are fundamentally difficult to identify via X-ray mammography. In addition, in the classic "fluoroscopic mammography", the problem exists that lesions are covered by other tissue structures and as a result are poorly recognized or localized.

In order to overcome these disadvantages, it is known to carry out a contrast-enhanced dual-spectrum mammography or CEDEM (contrast enhanced dual energy mammography) after an intravenous administration of contrast medium such as iodine. Hereby, while maintaining a breast compression, a high-energy recording is carried out followed by a low-energy recording or vice versa. Subsequently, by way of a registration and a weighted subtraction, a creation of a recombined resultant image takes place in which substantially the regions in which the contrast medium has become concentrated are particularly clearly visible. Carcinomas, in particular, are distinguished in that due to their increased vascularization (neoangiogenesis) and increased vascular permeability, they concentrate contrast medium more strongly. Thus, with dual-spectrum mammography, the iodine contrast can be maximized and the otherwise occult tumor can be made visible.

The X-ray radiation energies for the high energy and the low energy recordings are typically selected such that the value of the lower energy lies in the vicinity of the energy value of the (X-ray) absorption edge of the contrast medium used for X-ray radiation and the value of the higher energy lies far above the energy value of this absorption edge. For example, the K-absorption edge of the contrast medium iodine for X-ray energy, herein also called the X-ray absorption edge for short, is at 33.17 keV. Other contrast media are also conceivable, e.g. silver-containing substances.

3D breast tomosynthesis offers an imaging method in which the breast is recorded from many different angles. For example, recordings are made at angles from 15 to 50 degrees. In total, for example between 9 and 25 recordings are made from different angles at low dose, so that the overall dose approximately corresponds to that of a classic two-dimensional mammography recording. From the acquired projection data, images are calculated for individual slices of the breast tissue; in total, a three-dimensional image data set can arise which approximates to a computed tomography recording. For the reconstruction of a three-dimensional image of a region to be examined from the acquired projection scan data, for example, the method of filtered back projection is used. The resulting three-dimensional image can be observed for diagnostic purposes slice-wise or coherently. Since, during appraisal, slices above and below the respective slice selected for display can be hidden, tissue changes can be more easily identified.

The calculation of a recombined dual-energy mammogram from 3D breast tomosynthesis (CEDET) is also known. In this method, a high energy tomosynthesis recording and a low energy tomosynthesis recording are made and a difference image is determined from the two recordings.

In order to confirm the malignancy of a radiologically identified tumor, a biopsy can be carried out with the aim of a laboratory diagnostic appraisal. This typically takes place at a later time point separately from the radiological examination.

SUMMARY

The inventors have discovered that a conventional biopsy which is carried out using soft, that is, low energy X-ray radiation with X-ray imaging carries with it the renewed risk that the lesion to be biopsied is not identified and cannot be biopsied precisely. The inventors have further discovered that a biopsy with the simultaneous making of dual energy recordings with contrast medium increases the medical risk for the patient due to the increased radiation dose.

At least one embodiment of the application provides an apparatus which enables a lesion to be reliably imaged and/or localized for, or during, a biopsy, with a low radiation burden for a patient. At least one embodiment of the application further monitors this position over the course of a biopsy.

At least one embodiment of the application is directed to a method for monitoring a tissue removal from breast tissue, via an X-ray imaging system, a corresponding computing unit, a corresponding X-ray imaging system, a corresponding computer program product and a corresponding computer-readable medium, according to the independent claims. Preferred and/or alternative, advantageous embodiment variants are the subject matter of the claims.

Inventive solutions to problems are described below, both in relation to the claimed method and also in relation to the claimed devices. Features, advantages or alternative embodiments mentioned herein are also transferable to the other claimed subject matter and vice versa. In other words, the present claims (which are directed, for example, to a method) can also be further developed with features that are described or claimed in conjunction with one of the devices.

The corresponding functional features of the method are thereby provided by corresponding modules or units.

The present application relates in a first embodiment to a method for monitoring a tissue removal via an X-ray imaging system, wherein the tissue removal from a lesion in a breast tissue that is to be examined takes place via a removal instrument. The method comprises:

acquiring first X-ray projection scan data, influenced by a contrast medium, of the breast tissue situated in an image field of the X-ray imaging system, resulting in contrast medium-influenced first X-ray projection scan data;

reconstructing a first image data set based upon the contrast medium-influenced first X-ray projection scan data acquired; and determining, based upon the first image data set reconstructed, a current position of the lesion in relation to a reference coordinate system, the contrast medium-influenced first X-ray projection scan data being generated with X-ray photons having a photon energy above an absorption edge of the contrast medium.

Another embodiment of the present invention relates to a computing unit for monitoring a tissue removal via an X-ray imaging system, wherein the tissue removal takes place via a removal instrument from a lesion in a breast tissue that is to be examined, having at least one processor for carrying out the inventive method. Advantageously, the computing unit is integrated into the X-ray imaging system. Alternatively, the computing unit can also be arranged separately or remotely therefrom.

The computing unit can be configured, in particular, to carry out the step of determining the current position of the lesion, but also to carry out the entire embodiment of the inventive method, for the X-ray imaging system or for a plurality of systems, e.g. in a radiology center or hospital having a plurality of magnetic resonance systems.

Another embodiment of the present invention relates to an X-ray imaging system for monitoring a tissue removal, wherein the tissue removal takes place from a lesion in a breast tissue that is to be examined, via a removal instrument. The X-ray imaging system comprises an X-ray radiation source to emit X-ray photons;

an acquisition unit to acquire first X-ray projection scan data, influenced by a contrast medium, of the breast tissue situated in an image field of the X-ray imaging system, resulting in contrast medium-influenced first X-ray projection scan data;

a reconstruction unit for reconstructing a first image data set based upon the contrast medium-influenced first X-ray projection scan data acquired; and a determination unit to determine, based upon the first image data set reconstructed, a current position of the lesion in relation to a reference coordinate system.

The X-ray radiation source is configured to emit X-ray photons which have a photon energy above an absorption edge of the contrast medium used. These X-ray photons are used for generating the contrast medium-influenced first X-ray projection scan data.

A further embodiment of the present invention relates to a computer program product with a computer program which is directly loadable into a memory storage unit of an X-ray imaging system, having program portions in order to carry out the steps of an embodiment of the inventive method when the computer program is executed in the X-ray imaging system.

A further embodiment of the present invention relates to a computer-readable medium on which program portions that can be read in and executed by a computing unit are stored, in order to carry out all the steps of an embodiment of the inventive method when the program portions are executed by the computing unit of the X-ray imaging system. Advantageously, in particular, the determination of the current position of the lesion or the determination of the removal trajectory can be carried out on a computer, for example, in the computing unit of the X-ray imaging system.

A further embodiment of the present invention relates to a computing unit for monitoring a tissue removal via an X-ray imaging system, wherein the tissue is removal, via a removal instrument, from a lesion in a breast tissue to be examined, the computing unit comprising:

at least one processor, configured to acquire first X-ray projection scan data, influenced by a contrast medium, of the breast tissue situated in an image field of the X-ray imaging system, resulting in contrast medium-influenced first X-ray projection scan data;

reconstruct a first image data set based upon the contrast medium-influenced first X-ray projection scan data acquired; and determine, based upon the first image data set reconstructed, a current position of the lesion in relation to a reference coordinate system, the contrast medium-influenced first X-ray projection scan data being generated with X-ray photons having a photon energy above an absorption edge of the contrast medium.

BRIEF DESCRIPTION OF THE DRAWINGS

The above-described properties, features and advantages of this invention and the manner in which they are achieved are made more clearly and distinctly intelligible with the following description of the example embodiments which are described in greater detail making reference to the drawings. This description entails no limitation of the invention to these example embodiments. In different figures, the same components are provided with identical reference signs. The drawings are in general not to scale. In the drawings.

DETAILED DESCRIPTION OF THE EXAMPLE EMBODIMENTS

Figure 1:
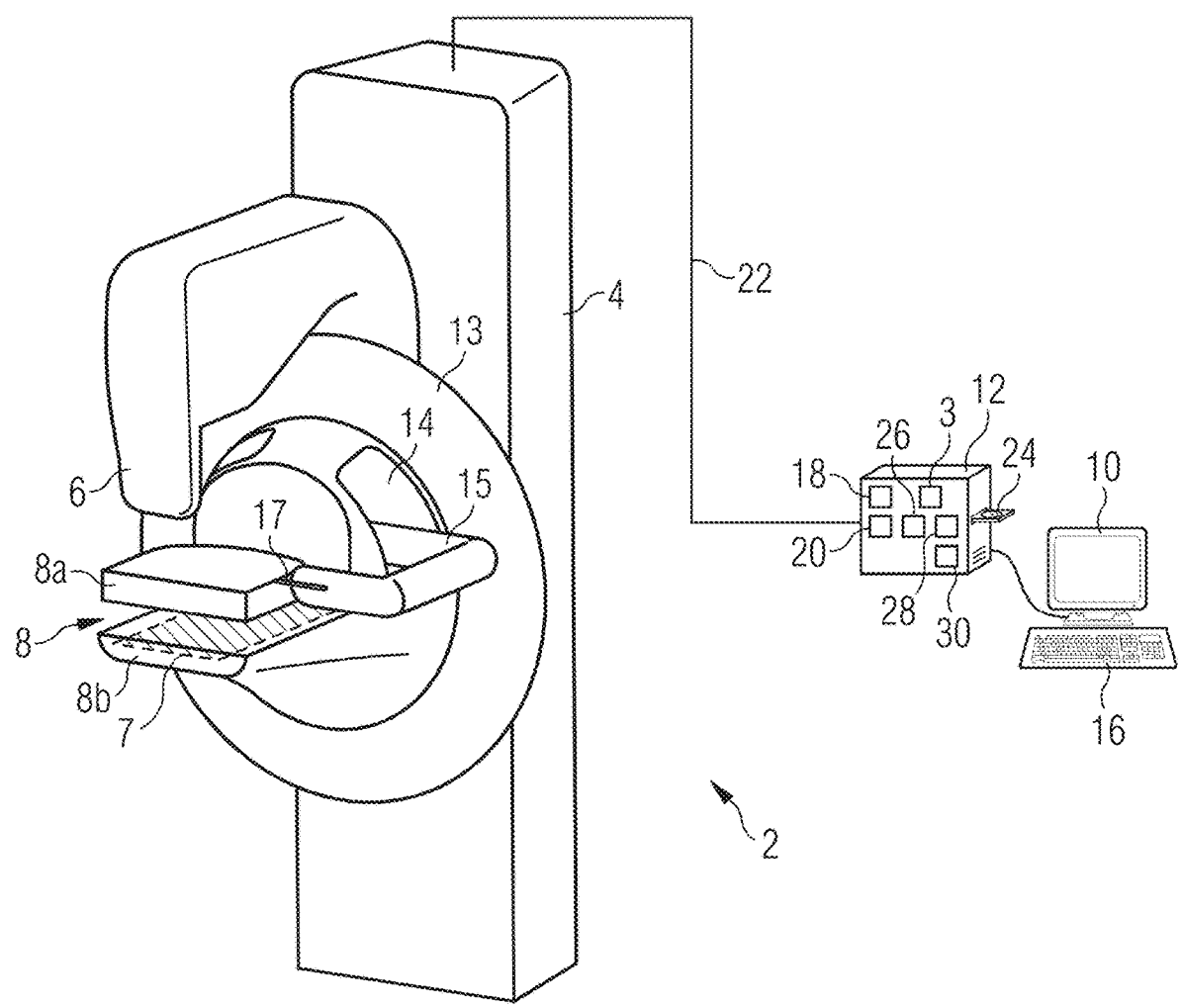
FIG. 1 shows a view of an X-ray imaging system in the form of a mammography system comprising a computing unit, respectively according to an embodiment of the present invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules.

Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The present application relates in a first embodiment to a method for monitoring a tissue removal via an X-ray imaging system, wherein the tissue removal from a lesion in a breast tissue that is to be examined takes place via a removal instrument. The method comprises:

acquiring first X-ray projection scan data, influenced by a contrast medium, of the breast tissue situated in an image field of the X-ray imaging system, resulting in contrast medium-influenced first X-ray projection scan data;

reconstructing a first image data set based upon the contrast medium-influenced first X-ray projection scan data acquired; and determining, based upon the first image data set reconstructed, a current position of the lesion in relation to a reference coordinate system, the contrast medium-influenced first X-ray projection scan data being generated with X-ray photons having a photon energy above an absorption edge of the contrast medium.

A tissue removal corresponds to a biopsy in which a part of a tissue, for example a tumor tissue, is removed from a body of an examination object. For this purpose, a removal instrument, for example, a biopsy needle, is used. Reference should explicitly be made to the step of tissue removal itself not being included by the embodiment of the inventive method. Rather, the embodiment of the inventive method is designed to be carried out simultaneously and/or in parallel with a tissue removal. It can also be provided that individual steps of embodiments of the inventive method are carried out interleaved with steps of the tissue removal. However, the embodiment of the inventive method and the tissue removal themselves are to be regarded as separate from one another.

Breast tissue can include female or male breast tissue.

A first step in an embodiment relates to an acquisition of first X-ray projection scan data that is influenced by a contrast medium or is contrast medium-influenced or contrast medium-supported, of the breast tissue situated in an image field of the X-ray imaging system. In other words, the breast tissue to be examined which comprises a lesion is irradiated with X-ray photons. The X-ray attenuation according to the tissue distribution in the breast tissue and the irradiation direction is acquired via the first X-ray projection scan data.

Projection scan data that should be understood as influenced by a contrast medium or as contrast medium-supported have been recorded after administration of a contrast medium and its transport into the examination region, that is, the breast tissue to be examined. Preferably, iodine is used as the contrast medium. Other contrast media are also possible and within the purpose of the invention. The selection of a suitable contrast medium can depend, for example, on the type of lesion, intolerances and/or anatomical peculiarities of the patient or suchlike. On selection of another contrast medium, it can also be suitable or required to adapt filter materials or the X-ray tube spectrum used.

A further step in an embodiment relates to a reconstruction of a first image data set based upon the acquired X-ray projection scan data. In this step, the first X-ray projection scan data is converted into a digitally reproducible image in the form of the first image data set.

An image reconstruction should be understood in this context to be a determination of an image representation on the basis of the acquired scan data. Acquired two-dimensional scan data can mean, for example, a simple processing, in particular, an interference elimination or correction of the available scan data that already contain an image representation. However, in the case of a recording of projection scan data from different directions, the image reconstruction can also comprise the reconstruction of a three-dimensional representation.

A further step the embodiment of relates to a determination, based upon the reconstructed first image data set, of a current position of the lesion in relation to a reference coordinate system.

The reference coordinate system should be understood as the reference coordinate system of the X-ray imaging system with which the X-ray projection scan data is acquired. It can also represent the coordinate system in which the removal instrument moves. The determination of the current position of the lesion can take place, firstly, manually through an operator on the basis of the first image data set, for example, via a marking of at least one position via mouse-cursor interaction. Alternatively or additionally, for example, by way of a semi-automatic method, the lesion can be localized automatically by way of an image analysis method. For this, for example, pixel values of individual pixels can be compared with a threshold value and accordingly assigned to the lesion or the surrounding tissue. Also possible is the use of algorithms for determining edge pixels of the lesion. The determination of the current position of the lesion can also comprise a determination of the size, the volume and/or the extent of the lesion in at least one spatial dimension.

In an embodiment of the inventive method, the contrast medium-influenced first X-ray projection scan data are generated with X-ray photons which have a photon energy above an absorption edge of the contrast medium used.

The (X-ray) photon energy or X-ray beam energy usually defines the mean energy of the X-ray quantum energy spectrum of the emitted X-ray photons. For example, with an X-ray tube voltage of an X-ray radiation source for a mammography recording of 30 kV, the mean energy of the X-ray radiation spectrum is approximately 20 keV. The X-ray energy spectrum should be understood as the energy distribution of the X-ray quanta generated and emitted by an X-ray tube.

Typically, X-ray beams emitted from an X-ray radiation source do not have only one discrete energy, but a whole spectrum of different energy values. Thereby, in addition to the specified mean value of the energy distribution, an energy value e*U can be assigned to the emitted X-ray radiation, which defines a minimum wavelength or a maximum energy of the X-ray quanta of the X-ray radiation (this value would be 30 keV in the example given and should be mentioned here purely for better differentiation). In this regard, the expressions "high" and "low" should be understood with regard to X-ray radiation with high energy and low energy relative to the energy of the X-ray absorption edge of the contrast medium used.

An embodiment of the inventive procedure is based upon the acknowledgement that a good or sufficient image contrast between a lesion, in particular a tumor and the surrounding mammary tissue can be achieved by way of high energy X-ray photons. In other words, X-ray photons which have a photon energy above the X-ray absorption edge, also known as the K-edge, achieve an image contrast which is sufficient for a use for a biopsy or tissue removal. In other words, the first image data set is based exclusively on high-energy X-ray projection scan data, wherein the X-ray photons have a photon energy above the specific X-ray absorption edge of the contrast medium used. This procedure advantageously dispenses with the acquisition of low-energy X-ray projection scan data and the higher radiation dose for the patient associated therewith and is nevertheless suitable for clearly imaging and/or to localizing a lesion.

Another embodiment of the present invention relates to a computing unit for monitoring a tissue removal via an X-ray imaging system, wherein the tissue removal takes place via a removal instrument from a lesion in a breast tissue that is to be examined, having at least one processor for carrying out the inventive method. Advantageously, the computing unit is integrated into the X-ray imaging system. Alternatively, the computing unit can also be arranged separately or remotely therefrom.

The computing unit can be configured, in particular, to carry out the step of determining the current position of the lesion, but also to carry out the entire embodiment of the inventive method, for the X-ray imaging system or for a plurality of systems, e.g. in a radiology center or hospital having a plurality of magnetic resonance systems.

Another embodiment of the present invention relates to an X-ray imaging system for monitoring a tissue removal, wherein the tissue removal takes place from a lesion in a breast tissue that is to be examined, via a removal instrument. The X-ray imaging system comprises an X-ray radiation source to emit X-ray photons;

an acquisition unit to acquire first X-ray projection scan data, influenced by a contrast medium, of the breast tissue situated in an image field of the X-ray imaging system, resulting in contrast medium-influenced first X-ray projection scan data;

a reconstruction unit for reconstructing a first image data set based upon the contrast medium-influenced first X-ray projection scan data acquired; and a determination unit to determine, based upon the first image data set reconstructed, a current position of the lesion in relation to a reference coordinate system.

The X-ray radiation source is configured to emit X-ray photons which have a photon energy above an absorption edge of the contrast medium used. These X-ray photons are used for generating the contrast medium-influenced first X-ray projection scan data.

The X-ray imaging system can advantageously also comprise an establishing unit for establishing a removal trajectory for the removal instrument, which intersects the determined position of the lesion.

The acquisition unit can be configured as a directly or indirectly converting X-ray radiation detector. The acquisition unit can also be configured as an interface of a computing unit of the X-ray imaging system for further processing the X-ray projection scan data, via which interface the scan data is transferred to the computing unit.

The acquisition unit, the reconstruction unit and the establishing unit can be included by the computing unit of the X-ray imaging system. They can each be configured as single or multiple components, that is, as a processor or a computer which can also be arranged spatially coherently or spatially separately from one another.

The X-ray imaging system can advantageously also include the removal instrument. It can also include a display device on which a reconstructed image data set, for example, of the first image data set can be displayed for an observer. Particularly preferably, the X-ray imaging system is configured as a mammography system.

A further embodiment of the present invention relates to a computer program product with a computer program which is directly loadable into a memory storage unit of an X-ray imaging system, having program portions in order to carry out the steps of an embodiment of the inventive method when the computer program is executed in the X-ray imaging system.

A further embodiment of the present invention relates to a computer-readable medium on which program portions that can be read in and executed by a computing unit are stored, in order to carry out all the steps of an embodiment of the inventive method when the program portions are executed by the computing unit of the X-ray imaging system. Advantageously, in particular, the determination of the current position of the lesion or the determination of the removal trajectory can be carried out on a computer, for example, in the computing unit of the X-ray imaging system.

In a preferred embodiment of the invention, a determination of a removal trajectory for the removal instrument, which includes the determined current position of the lesion, takes place. This step takes account of a starting position of the removal instrument and the current position of the lesion. The removal trajectory defines a movement path for the removal instrument on which the removal instrument intersects, meets or crosses the lesion at least once in order to remove tissue there. Preferably, the removal trajectory is configured straight. The determination of a removal trajectory can take place automatically via a computing unit or manually by an operator.

In a preferred embodiment of the invention, the X-ray photons are emitted by an X-ray radiation source of the X-ray imaging system to which a voltage in the range of 40 kV to 49 kV is applied. X-ray tube voltages within this range produce an X-ray photon energy spectrum the mean energy of which lies above, preferably far above the X-ray absorption edge of the contrast medium iodine. Voltage values within this range cause a mean photon energy in the range of approximately 30 keV to 40 keV. This additionally depends on the selection or configuration of the X-ray radiation filter. Herein, a titanium or copper filter is typically provided. In this embodiment, a titanium filter would have, for example, a thickness of 0.4 mm to 1.4 mm, and a copper filter would be thinner. According to a particularly preferred embodiment of the invention, the X-ray tube voltage is in the range from 45 kV to 49 kV. Voltage values within this range cause a mean photon energy of approximately 35 keV to 40 keV. Test have shown that this mean photon energy brings about a particularly good contrast between the lesion and the surrounding breast tissue in the first image data set.

In another advantageous embodiment of the present invention, the first image data set comprises at least two two-dimensional or one three-dimensional image data set. In other words, the first image data set can be configured as a contrast medium-supported stereo mammography (recording). In this case, projection scan data is acquired from two viewing directions slightly offset from one another toward the breast tissue and are reconstructed independently of one another into two-dimensional single images. From these, the depth information can then be extracted, for example, by triangulation. Alternatively, for this purpose, the projection scan data acquisition can comprise the contrast medium-supported recording of projections in a plurality of different viewing directions which together are reconstructed to a three-dimensional tomosynthesis image data set. Herein, the depth information is then obtained directly by way of the depth coordinates of the slice image comprising the lesion. The selection of the configuration of the first image data set can depend, in particular, on the capacities of the X-ray imaging system used and alternatively or additionally, the type of breast tissue to be examined or the lesion can require a stereo mammography or a tomosynthesis.

In a further advantageous embodiment of the present invention, before the acquisition of the first X-ray projection scan data, scout projection scan data influenced by the contrast medium is acquired. The scout projection scan data preferably covers a larger image field than the first X-ray projection scan data. The image field should be understood as the field of view (FoV) of the X-ray imaging system. The scout projection scan data serves for an identification and the first coarse localization of the lesion in the breast tissue and possibly also an orientation or adaptation of the image field of the X-ray imaging system to the lesion. In other words, it can be provided that the examination object is repositioned on the basis of a scout recording reconstructed from the scout projection scan data in order subsequently actually to acquire the lesion with the first projection scan data. The field of view is preferably reduced for the acquisition of the first X-ray projection scan data according to the size of the lesion, so that the lesion can be imaged as well as possible with the first image data set.

In a further advantageous embodiment of the present invention, the current position of the lesion in the first image data set is registered before the determination of the removal trajectory with a reference position of the lesion in a reference image data set. Typically, at the time point of a tissue removal and the execution of the inventive method, a radiological diagnosis with regard to the lesion in the breast tissue to be examined is already available. In other words, for example, at least one dual-spectrum mammography or a tomosynthesis recording of the breast tissue including the lesion, each of which can function as a reference image data set, is available. It is thus provided according to the invention to register the lesion in the first image data set with the reference position of the lesion in the reference image data set according to the radiological diagnosis. In other words, this step brings about an imaging of the lesions in both the image data sets. For this purpose, an arbitrary per se known and suitable registration method can be used. For example, in mammography, the following methods are particularly suitable: elastic or deformable (non-rigid) registration, multi-resolution registration, feature-based registration or suchlike. In the registration, at least image information relating to the lesion is taken into account. By registration of the first image data set with the reference image data set, the determination of the position of the lesion in the first image data set can be optimized and/or confirmed, since in this way information relating to the position of the lesion of the reference image data set, which can be lacking in the first image data set, can be taken into account for the position determination.

According to a particularly preferred embodiment, for the registration, the position of at least one anatomical landmark is taken into account in the first image data set and the reference image data set. Since a preliminary recording, that is, a reference image data set can have been carried out with a (slightly) different compression of the breast tissue, a registration while taking account of additional anatomical landmarks which are included in the first image data set is particularly useful in order to increase the registration accuracy and thereby further to improve the position determination. In mammography, anatomical landmarks can be, in particular, the skin line of the breast tissue, the mamilla, relatively large blood vessels and/or microcalcification or suchlike. In other words, it is provided in this embodiment that apart from image information regarding the lesion, image information regarding at least one anatomical landmark, preferably a plurality of anatomical landmarks for an overlaying of the first image data set with the reference image data set is taken into account.

In a further advantageous embodiment of the invention, at least at one time point second X-ray projection scan data influenced by the contrast medium is acquired and reconstructed to a second image data set, while the removal instrument completes a movement along the removal trajectory. In other words, at least once, preferably multiple times at different time points after the determination of the removal trajectory, based on the position of the lesion, a second image data set is reconstructed. This procedure serves for monitoring the movement of the removal instrument along the removal trajectory. If, during the movement, unexpected deviations, for example if an unforeseeable patient movement should occur, the movement of the removal instrument can be interrupted thereby and thus an injury to the patient prevented.

In a further advantageous embodiment of the invention, third X-ray projection data influenced by the contrast medium is acquired and reconstructed to a third image data set once the removal instrument has completed the movement along the removal trajectory. This procedure serves for checking the breast tissue and/or the lesion and enables monitoring that a tissue sample has indeed been taken from the lesion and/or that no injuries have been caused by the removal instrument.

Particularly advantageously, the first, the second and/or the third image data set are displayed to an operator instantaneously. Preferably, all three image data sets are displayed to the operator. In this way, visual monitoring can be ensured throughout the entire biopsy process. In this embodiment, instantaneously includes a substantially temporally undelayed or barely delayed image display, so that where required, a rapid reaction, for example, an interruption of the movement of the removal instrument can be effected. This embodiment self-evidently also comprises an instantaneous or semi-instantaneous image reconstruction.

FIG. 1 shows a view of an X-ray imaging system in the form of a mammography system 2 comprising a computing unit 12, respectively according to an embodiment of the present invention. The inventive mammography system 2 has a housing 13 with at least one opening 14. The housing 13 is linked to a main body 4 of the system 2. Arranged on the side of the housing 13 facing away from the main body 4 is a compression unit 8 consisting of the compression element 8a and the object table 8b such that an object situated in the compression unit 8, for example, in the form of a breast tissue, can be transirradiated with an X-ray radiation source 6. The X-ray radiation is detected with an acquisition unit in the form of an X-ray radiation detector 7 in the region of the object table 8b. The mammography system 2 shown here also comprises a biopsy unit 15. This partially protrudes from an opening 14 of the housing 13. The opening 14 can be larger than shown, so that it permits, for example, a pivot movement of ±90° about an axis or can be displaceable in the housing 13 in order to permit a corresponding pivot movement. Alternatively, the biopsy unit 15 can also be arranged with a vertical orientation. The removal unit 15 is partially arranged outside the housing 13 and comprises at its movable end a removal instrument in the form of a biopsy needle 17.

The mammography system 2 has a computing unit in the form of a computer system 12 which is configured as a computer and is linked to a display unit 10, for example, for graphical display of reconstructed mammography image data BD1, BD2, BD3 and an input unit 16. The display unit 10 can be, for example, an LCD, plasma or OLED screen. It can also be a touch-sensitive screen which is configured as an input unit 16. Such a touch-sensitive screen can be integrated into the imaging device or can be configured as part of, or itself as, a mobile device. The input unit 10 is, for example, a keyboard, a mouse, a so-called touch screen or a microphone for speech input. The input unit 16 can also be configured to recognize movements of an operator and to convert them into corresponding commands.

Figure 2:
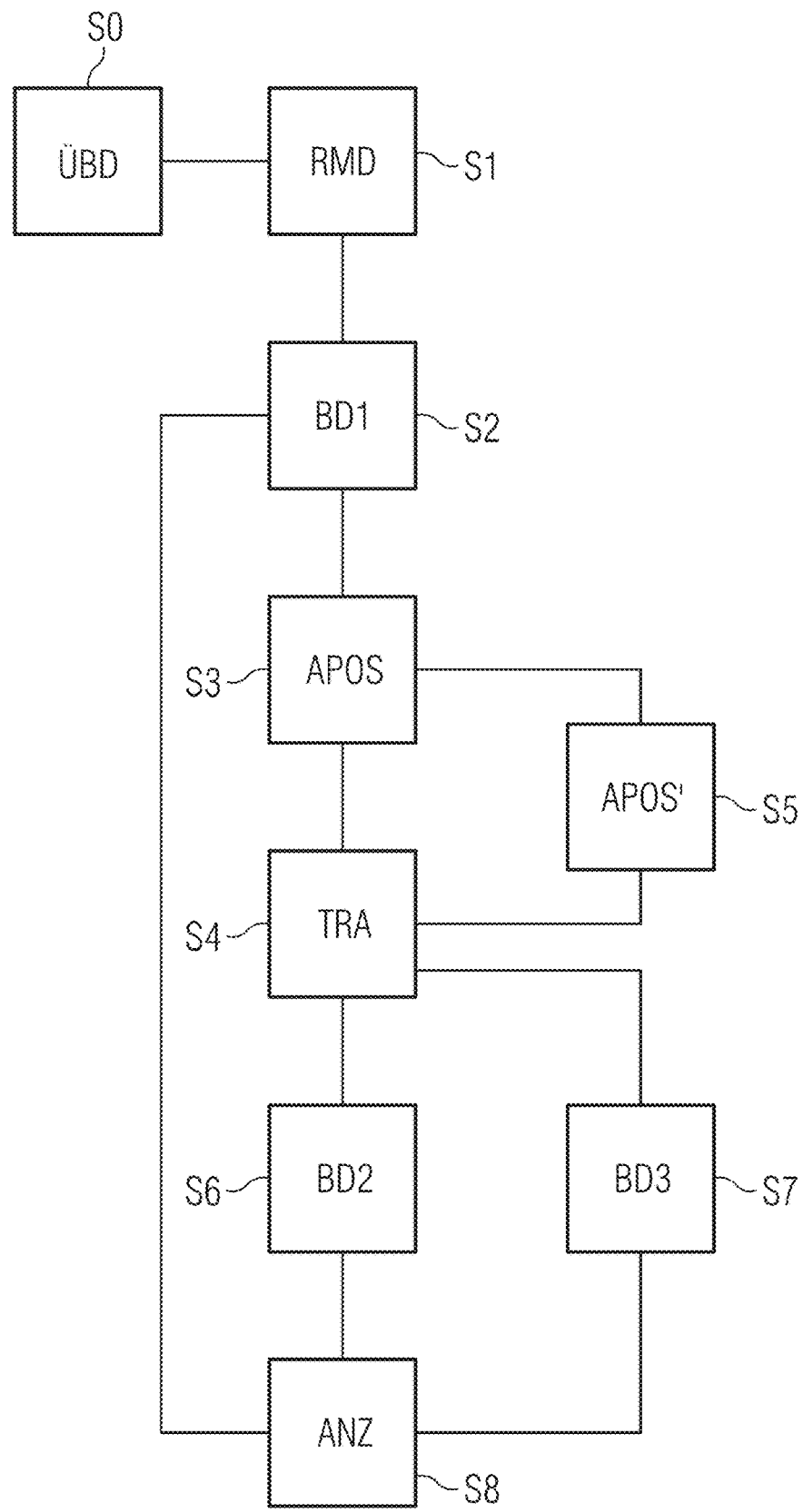
FIG. 2 shows a schematic representation of an inventive method according to an example embodiment of the present invention.

The computer system 12 is configured to carry out an embodiment of the inventive method as described in greater detail, for example, by reference to FIG. 2. For this purpose, the computer system 12 is linked to the main body, for example, of the base unit 4 of the mammography system 2 for data exchange. For example, control signals for the system 2 for the mammography examination can be transferred from the computer system 12 to the base unit 4. For this purpose, for example, different scan protocols, each matched to an examination type, can be stored in a memory store 18 and selected by an operator, for example, a doctor or personnel trained in medical technology, before the scan as appropriate to a medical problem. At the same time, recorded X-ray projection scan data RPM is transferred for an inventive further processing in the computer system 12 by the mammography system 2. The connection 22 is realized via corresponding interfaces cable-bound or cable-free in a known manner.

The computer system 12 comprises a plurality of units.

The computer system 12 comprises an acquisition unit 20. The acquisition unit 20 can be configured as a data interface and serves to acquire X-ray projection scan data RMD from the main body 4 in the computer system 12 and possibly to store it in a memory store 18 and/or to feed it to a reconstruction unit 28.

The computer system 12 further comprises a reconstruction unit 28. This is configured to transfer the X-ray projection scan data RPM according to the selected scan protocol into the image data sets BD1, BD2, BD3. Herein, data preparation steps and artifact corrections can also be included. The reconstruction rules are per se known and therefore need no further description.

The computer system 12 further comprises a determination unit 30. This is configured to determine the current position APOS of a lesion L in the breast tissue BG to be examined. The current position APOS is determined in relation to the reference coordinate system of the mammography system 2 which, in this embodiment, is also the reference coordinate system of the removal instrument 17. The determination unit 30 is further configured, if relevant, to carry out a segmentation of the lesion in order to determine the current position in the reconstructed image data, in this case the first image data set BD1. For this purpose, the determination unit 30 can also be configured to register the current position APOS of the lesion L with a reference position in a reference image data set. The reference image data set can thereby be available from a previous radiological examination of the same examination object with regard to the breast tissue BG and recallable in a PACS, RIS or HIS of a medical device and/or the memory store 18 of the mammography system 2.

The computer system 12 can further optionally comprise an establishing unit 26. This is configured, on the basis of the determined current position APOS of the lesion L, to determine a removal trajectory TRA for the removal instrument 17 which can be accomplished via the biopsy unit 15, in order to obtain a tissue sample of the lesion L. The removal trajectory TRA is characterized in that it intersects or meets the current position APOS of the lesion and/or the lesion L at least once. Alternatively, the removal trajectory can be determined manually by an operator.

In the present case, in particular, the named units 26, 28 and 30 are configured as separate modules within the computer system 12 which, where required, exchange data with one another. Alternatively, all the units named can be integrated as a computing unit, whether in the form of a physical or a functional integrity.

The computer system 12 can cooperate with a computer-readable data carrier 24, in particular, in order to carry out an embodiment of an inventive method via a computer program with program code. Furthermore, the computer program can be retrievably stored on the machine-readable carrier 24. In particular, the machine-readable carrier 24 can be a CD, DVD, Blu-Ray disk, a memory stick or a hard disk drive.

In particular, the units 26, 28 and 30 can be configured in the form of hardware or software. For example, the units are configured as FPGAs (Field Programmable Gate Arrays) or comprise an arithmetic logic unit.

At least one computer program which carries out all the method steps of an embodiment of the inventive method when the computer program is carried out on the computer 12 can be stored in the memory store 18 of the computer system 12. The computer program for carrying out the method steps of an embodiment of the inventive method comprises program code. Furthermore, the computer program can be configured as an executable file and/or can be stored on a computer system other than the computer system 12. For example, the mammography system 2 can be configured so that the computer system 12 loads the computer program for carrying out an embodiment of the inventive method via an Intranet or the Internet into its internal working memory. Alternatively, it can be provided that the computer system 12 is itself part of an Internet or Intranet, for example, of an HIS (Hospital Information System) or an RIS (Radiology Information System) and has access to different mammography systems 2 of a medical institution in order to carry out an embodiment of the inventive method centrally for different systems 2.

FIG. 2 shows a schematic representation of an embodiment of an inventive method according to an example embodiment of the present invention. The method comprises a plurality of steps.

In a first step S1, the acquisition of first X-ray projection scan data RMD takes place. The acquisition comprises both an acquisition of X-ray radiation via an X-ray radiation detector 7 as well as an acquisition of the X-ray projection scan data RMD in the computer system 12. The X-ray projection scan data comprises at least two X-ray projections from two different viewing directions. In other words, in this step, the X-ray radiation source 6 and the X-ray radiation detector 7 are pivoted together at least once relative to the breast tissue BG to be examined. It is characteristic for this step that a contrast medium, preferably iodine, has become concentrated in the breast tissue to be examined. For this purpose, the examination object can previously have received a contrast medium. It is further characteristic that the X-ray photons which are used for the creation of the X-ray projection scan data, have a (mean) quantum energy which lies above the X-ray absorption edge of the contrast medium. This brings about a good intrinsic image contrast between the lesion and the surrounding breast tissue, so that purely based on this first X-ray projection scan data RMD, a current position APOS can be established.

High-energy X-ray radiation in the context of an embodiment of the invention should be understood as X-ray radiation which has a mean quantum energy in relation to the emitted energy spectrum which lies above the X-ray absorption edge of the contrast medium. In order to achieve this, the X-ray radiation source 6 is preferably operated with a tube voltage of between 40 and 49 kV, preferably 45 to 49 kV.

Optionally, a step S0 can be provided. In this step, following a contrast medium administration, the acquisition of scout projection scan data which is reconstructed to a scout image data set ÜBD takes place and is preferably displayed to the operator via the display unit 10. This scout recording has an enlarged field of view as compared with the first image data set BD1 and serves for a coarse localization of the lesion L in the breast tissue BG. The scout image data set ÜBD preferably covers the whole breast. On the basis of the scout recording ÜBD, a new positioning of the breast tissue BG in the compression unit 8 or a new positioning or setting of the X-ray radiation source 6, in particular, the included collimator and/or the X-ray radiation detector 7 can take place. The scout recording ÜBD can be configured, in particular, as a tomosynthesis image data set which advantageously permits a slice-wise overview of the breast tissue in three dimensions.

In a further step S2, an image reconstruction takes place from the first projection scan data RMD in a per se known manner. From this, a first image data set BD1 is generated, as shown by way of example in FIG. 3 on the right side. The manner of the reconstruction can be adapted, in particular, to the type of the first X-ray projection scan data RMD. If these comprise, for example, a plurality of projection scan data from a plurality of different viewing directions, different slices of a particular spacing and overall a three-dimensional data set are calculated therefrom.

Figure 3:
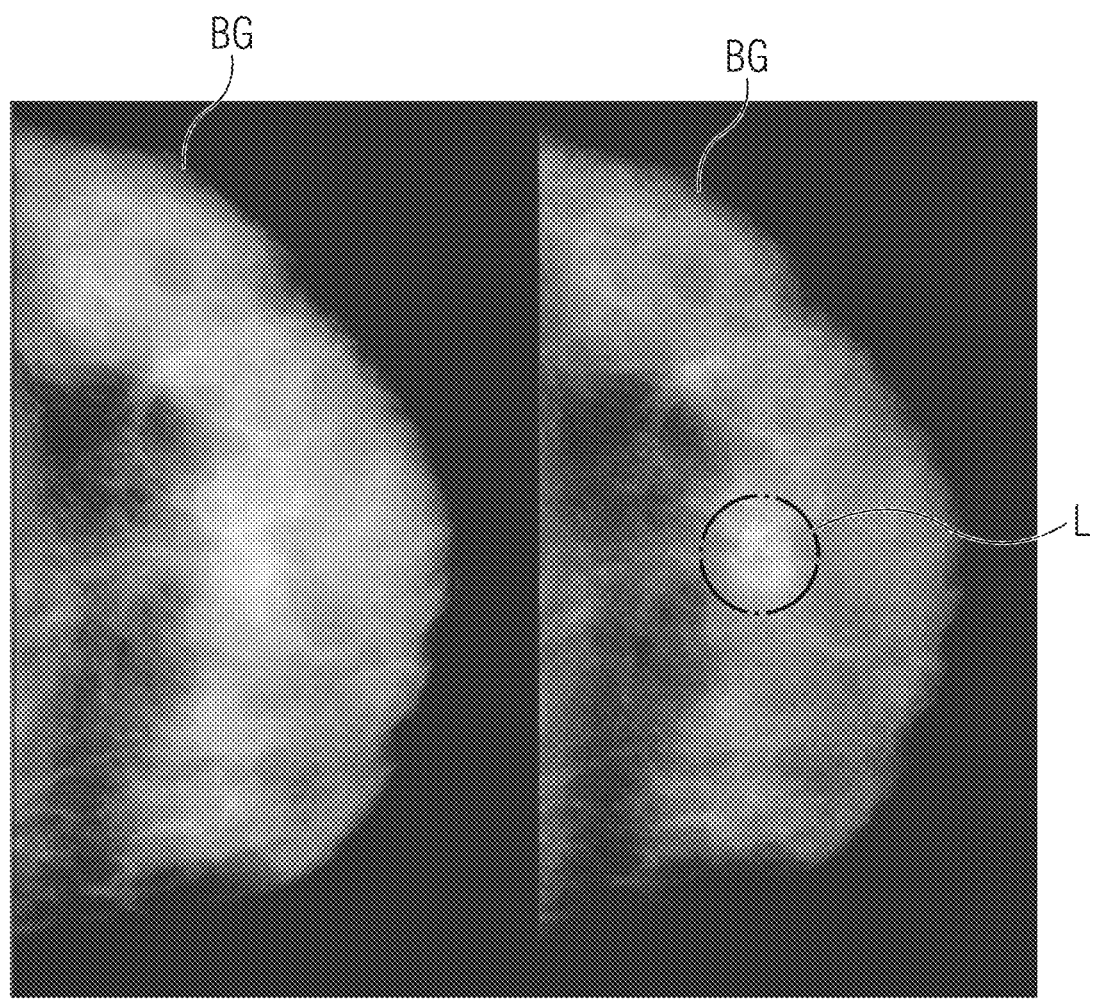
FIG. 3 shows a first image data set according to the prior art and an embodiment of the present invention.

FIG. 3 shows a comparison of mammography image data according to an embodiment of the prior art and an embodiment of the present invention. At left, breast tissue BG containing a lesion L is shown which has been imaged with low-energy X-ray radiation using a contrast medium. The lesion L is poorly visible and still less well distinguishable from the surrounding tissue BG. At right, by contrast, the same breast tissue BG has been imaged using high-energy X-ray radiation. Here, the lesion L is significantly lighter than the surrounding breast tissue BG, so that a position/size and/or volume determination is clearly significantly facilitated.

In a further step S3, the determination of the current position APOS of the lesion L takes place in the first image data set BD1 in relation to the reference coordinate system of the mammography system 2, in particular, the depth but also its extent and/or its volume is determined. For this purpose, an intensity-based and/or gradient-based segmentation can be provided in order to identify all the image elements, pixels or voxels that belong to the lesion L. The position determination can alternatively or additionally be based upon operator input, for example, manual markings via mouse and cursor in the first image data set BD1 shown.

In a further optional step S5, a registration of the identified current position of the lesion with a reference position of the lesion in a reference image data set, for example, the available dual-energy subtraction image of a previous radiological diagnostic session can take place. In this way, the localization, that is, the current position APOS of the lesion L is either improved or merely confirmed. The registration can take place with identification and registration of at least one further anatomical landmark in the two image data sets to be registered, in order to establish a more accurate current position APOS' of the lesion. The anatomical landmarks can be, for example, the skin line, the mamilla, a blood vessel shape or microcalcification, where present.

By use of the current position APOS, APOS', subsequently in an optional step S4, a removal trajectory TRA and corresponding control signals for the removal unit 15 or the removal instrument 17 can be established. The removal instrument 17 follows this trajectory on a subsequent tissue removal from the lesion L. The removal trajectory TRA meets or crosses the current position APOS, APOS' at least once, preferably multiple times. Multiple intersection of the current position is advantageous, in particular, if the lesion is relatively large and tissue samples are to be taken from different regions of the lesion L, for example, its center and an edge region. This step can be carried out manually, or automatically by the computing unit.

It should again be noted explicitly that the tissue removal itself is not excluded from embodiments of the present invention.

In further optional steps S6 and S7, second and/or third X-ray projection scan data can be acquired anew and reconstructed to image data BD2 and BD3. The acquisition of the scan data and the reconstruction of the image data BD2 and BD3 each correspond to the configuration variant that has also been used for the first X-ray projection scan data and/or the first image data.

The second image data BD2 is generated during a movement of the removal instrument 17 along the removal trajectory TRA. It serves for monitoring the movement of the removal instrument 17 and enables a rapid manual intervention by the operator, for example, in the event of unforeseen patient movement. Preferably, at a plurality of time points within the movement of the removal instrument, second image data BD2 is generated. The third image data BD3 is generated after conclusion of the movement of the removal instrument 17, that is, after a removal of a tissue sample. It serves for checking the breast tissue for injuries and for monitoring whether tissue of the lesion L has actually been removed at the desired position.

Both second and also third image data sets BD2, BD3 are generated under the influence of contrast medium and therefore have an image contrast that is comparably as good in relation to the lesion L as the first image data set BD1.

All the processing steps described here fulfill the criterion that they are performed instantaneously or semi-instantaneously. In this way, an immediate display of the image data sets BD1, BD2, BD3 is enabled without a noticeable time delay.

In this respect, in a last step S8, a display of the image data sets BD1, BD2, BD3 is provided after their generation, so that the operator can analyze the image information rapidly and directly.

An embodiment of the present invention can be summarized briefly as follows:

An embodiment of the invention is based upon the recognition that lesions in breast tissue, in particular tumors, already provide good image contrast in a high-energy recording, which is sufficient for biopsy purposes. A high energy recording is generated with X-ray photons which have a (mean) quantum energy above the X-ray absorption edge of a contrast medium, preferably iodine. This brings about a greater contrast than in a standard mammography, which is typically carried out with X-ray voltages of between 25 kV and 35 kV. In this way, a reduced radiation dose, which in a high-energy recording is only 20% to 50% that of a standard mammography, is advantageously achieved for the patient. If, in addition as usual, a dual-energy subtraction recording is used as the scout image data set, the dose would be in the order of 120% to 150% of the dose of a standard mammography. In comparison with a conventional stereotactic biopsy monitoring, the dose is only 20% to 50%, and in comparison with a full dual-energy recording with weighted subtraction, the dose saving would even be substantially greater. Furthermore, a more rapid process of the biopsy and therefore a low level of susceptibility to movements of the breast tissue is the result.

Where it has not yet explicitly been set out, although useful and in the spirit of the invention, individual example embodiments, individual sub-embodiments or features thereof can be combined or exchanged with one another without departing from the scope of the present invention. Advantages of the invention described in relation to an example embodiment also apply without explicit mention, where transferable, to other example embodiments.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for monitoring a tissue removal via an X-ray imaging system, the tissue is removable, via a removal instrument, from a lesion in a breast tissue to be examined, comprising:
   acquiring first X-ray projection scan data, influenced by a contrast medium, of the breast tissue situated in an image field of the X-ray imaging system, resulting in contrast medium-influenced first X-ray projection scan data;
   reconstructing a first image data set based upon the contrast medium-influenced first X-ray projection scan data acquired; and
   determining, based upon the first image data set reconstructed, a current position of the lesion in relation to a reference coordinate system, the contrast medium-influenced first X-ray projection scan data being generated with X-ray photons having a photon energy above an absorption edge of the contrast medium, wherein the first image data set is based on exclusively high-energy X-ray projection scan data of the first X-ray projection scan data, the high-energy X-ray projection scan data being associated exclusively with X-ray photons having the photon energy above an absorption edge of the contrast medium.

2. The method of claim 1, further comprising:
   determining a removal trajectory for the removal instrument, wherein the removal trajectory intersects the current position of the lesion determined.

3. The method of claim 2, further comprising:
   registering the current position of the lesion in the first image data set before the determining of the removal trajectory, a reference position of the lesion being in a reference image data set.

4. The method of claim 3, wherein the registering the current position of the lesion in the first image data set is based on a position of at least one anatomical landmark in the first image data set and the reference image data set.

5. The method of claim 2, further comprising:
   acquiring second X-ray projection scan data influenced by the contrast medium and reconstructing a second image data set based on the second X-ray projection scan data, while the removal instrument completes a movement along the removal trajectory.

6. The method of claim 5, further comprising:
   acquiring third X-ray projection data, influenced by the contrast medium, and
   reconstructing to a third image data set, after the removal instrument has completed the movement along the removal trajectory.

7. The method of claim 6, wherein at least one of the first image data set, the second image data set and the third image data set are displayed for an operator instantaneously.

8. The method of claim 5, wherein at least one of the first image data set and the second image data set are displayed for an operator instantaneously.

9. The method of claim 2, wherein the X-ray photons are emitted by an X-ray radiation source of the X-ray imaging system, to which a voltage in a range from 40 kV to 49 kV is applied.

10. The method of claim 2, wherein the X-ray photons are emitted by an X-ray radiation source of the X-ray imaging system, to which a voltage in a range from 45 kV to 49 kV is applied.

11. The method of claim 2, wherein the first image data set includes at least two two-dimensional or one three-dimensional image data set.

12. The method of claim 2, further comprising:
   acquiring scout projection scan data influenced by the contrast medium before the acquiring of the first X-ray projection scan data.

13. The method of claim 2, wherein the first image data set is displayed for an operator instantaneously.

14. The method of claim 1, wherein the X-ray photons are emitted by an X-ray radiation source of the X-ray imaging system, to which a voltage in a range from 40 kV to 49 kV is applied.

15. The method of claim 1, wherein the X-ray photons are emitted by an X-ray radiation source of the X-ray imaging system, to which a voltage in a range from 45 kV to 49 kV is applied.

16. The method of claim 1, wherein the first image data set includes at least two two-dimensional or one three-dimensional image data set.

17. The method of claim 1, further comprising:
   acquiring scout projection scan data influenced by the contrast medium before the acquiring of the first X-ray projection scan data.

18. A memory storage unit of an X-ray imaging system, storing program portions to carry out the method of claim 1 when the program portions are executed by a processor of the X-ray imaging system.

19. A non-transitory computer-readable medium storing program portions, readable and executable by a processor of an X-ray imaging system, to carry out the method of claim 1 when the program portions are executed by the processor of the X-ray imaging system.

20. A computing unit for monitoring a tissue removal via an X-ray imaging system, wherein the tissue is removable, via a removal instrument, from a lesion in a breast tissue to be examined, the computing unit comprising:
   at least one processor, configured to
      acquire first X-ray projection scan data, influenced by a contrast medium, of the breast tissue situated in an image field of the X-ray imaging system, resulting in contrast medium-influenced first X-ray projection scan data;
      reconstruct a first image data set based upon the contrast medium-influenced first X-ray projection scan data acquired; and
      determine, based upon the first image data set reconstructed, a current position of the lesion in relation to a reference coordinate system, the contrast medium-influenced first X-ray projection scan data being generated with X-ray photons having a photon energy above an absorption edge of the contrast medium, wherein the first image data set is based on exclusively high-energy X-ray projection scan data of the first X-ray projection scan data, the high-energy X-ray projection scan data being associated exclusively with X-ray photons having the photon energy above an absorption edge of the contract medium.

21. An X-ray imaging system, comprising:
   the computing unit of claim 20; and
   an X-ray radiation source to emit X-ray photons.

22. The X-ray imaging system of claim 21, further comprising at least one of
   an establishing unit to establish a removal trajectory for the removal instrument, which intersects the position of the lesion determined; and
   a display unit for instantaneous display of the first, image data set for an operator.

23. An X-ray imaging system for monitoring a tissue removal, wherein the tissue is removable, via a removal instrument, from a lesion in a breast tissue to be examined, comprising
   an X-ray radiation source to emit X-ray photons;
   an acquisition unit to acquire first X-ray projection scan data, influenced by a contrast medium, of the breast tissue situated in an image field of the X-ray imaging system, resulting in contrast medium-influenced first X-ray projection scan data;
   a reconstruction unit for reconstructing a first image data set based upon the contrast medium-influenced first X-ray projection scan data acquired; and
   a determination unit to determine, based upon the first image data set reconstructed, a current position of the lesion in relation to a reference coordinate system, wherein the X-ray radiation source is configured to emit X-ray photons having a photon energy above an absorption edge of the contrast medium, the X-ray photons being used for generating the contrast medium-influenced first X-ray projection scan data, wherein the first image data set is based on exclusively high-energy X-ray projection scan data of the first X-ray projection scan data, the high-energy X-ray projection scan data being associated exclusively with X-ray photons having the photon energy above an absorption edge of the contract medium.

24. The X-ray imaging system of claim 23, further comprising at least one of
   an establishing unit to establish a removal trajectory for the removal instrument, which intersects the position of the lesion determined; and
   a display unit for instantaneous display of the first, image data set for an operator.

* * * * *